US008543191B2

(12) United States Patent
Stemmer (10) Patent No.: US 8,543,191 B2
(45) Date of Patent: Sep. 24, 2013

(54) METHOD TO ACQUIRE MEASUREMENT DATA OF A BREATHING EXAMINATION SUBJECT BY MAGNETIC RESONANCE TECHNOLOGY, AND ASSOCIATED COMPUTER PROGRAM

(75) Inventor: Alto Stemmer, Abenberg (DE)

(73) Assignee: Siemens Aktiengesellschaft, Munich (DE)

( * ) Notice: Subject to any disclaimer, the term of this patent is extended or adjusted under 35 U.S.C. 154(b) by 450 days.

(21) Appl. No.: 12/953,792

(22) Filed: Nov. 24, 2010

(65) Prior Publication Data

US 2011/0130644 A1     Jun. 2, 2011

(30) Foreign Application Priority Data

Nov. 27, 2009   (DE) .......................... 10 2009 055 960

(51) Int. Cl.
    *A61B 5/05*           (2006.01)
(52) U.S. Cl.
    USPC ........... 600/428; 600/407; 600/410; 600/427; 600/424
(58) Field of Classification Search
    USPC .......................... 600/407, 410, 427, 424, 428
    See application file for complete search history.

(56) References Cited

U.S. PATENT DOCUMENTS

| | | | |
|---|---|---|---|
| 7,480,527 B2* | 1/2009 | Deshpande et al. .......... | 600/413 |
| 2008/0211497 A1 | 9/2008 | Iwadate et al. | |
| 2009/0018433 A1 | 1/2009 | Kassai et al. | |

OTHER PUBLICATIONS

"Comparison of Respiratory Triggering and Gating Techniques for the Removal of Respiratory Artifacts in MR Imaging," Lewis et al., Radiology, vol. 160 (1986) pp. 803-810.
"Navigator-Echo-Based Real-Time Respiratory Gating and Triggering for Reduction of Respiratory Effects in Three-Dimensional Coronary MR Angiography," Wang, et al., Radiology, vol. 198 (1996) pp. 55-60.

* cited by examiner

*Primary Examiner* — Unsu Jung
*Assistant Examiner* — Joel Lamprecht
(74) *Attorney, Agent, or Firm* — Schiff Hardin LLP

(57) ABSTRACT

A method for the acquisition of measurement data of a breathing examination subject by magnetic resonance includes the following steps: (a) detect the physiological breathing signal of the examination subject with a breathing signal detection unit, (b) evaluate the detected breathing signal in an evaluation unit, (c) based on the evaluated breathing signal, calculate in a computer at least one parameter affecting the type of acquisition of measurement data by means of magnetic resonance, (d) detect a current physiological breathing signal with the breathing signal detection unit, (e) compare the last detected breathing signals with at least one trigger condition, (f) initiate the acquisition of measurement data using the calculated parameter from step (c) upon satisfaction of the trigger conditions from step (e), (g) repeat the steps (d) through (f) until all desired measurement data have been acquired, and (h) store and/or process the acquired measurement data in a memory and/or processing unit. After the evaluation of the detected breathing signal, at least one parameter of a following acquisition of measurement data is thus determined automatically without an input by an operator of the MR apparatus in use being required.

21 Claims, 6 Drawing Sheets

METHOD TO ACQUIRE MEASUREMENT DATA OF A BREATHING EXAMINATION SUBJECT BY MAGNETIC RESONANCE TECHNOLOGY, AND ASSOCIATED COMPUTER PROGRAM

BACKGROUND OF THE INVENTION

1. Field of the Invention

The present invention concerns a method to acquire measurement data of a breathing examination subject by means of magnetic resonance technology and an associated computer program 2. Description of the Prior Art Magnetic resonance technology (in the following the abbreviation MR stands for magnetic resonance) is a known technique with which images of the inside of an examination subject (for example) can be generated. Expressed simply, in an MR examination one or more MR measurements (data acquisition) are performed with the examination subject in a comparatively strong, static, for the most part homogeneous basic magnetic field (field strengths from 0.2 Tesla to 7 Tesla or more) in an MR apparatus, so that nuclear spins in the subject orient along the basic magnetic field. The basic magnetic field is also termed B0 field. Radio-frequency excitation pulses are radiated into the examination subject to trigger nuclear magnetic resonances, the triggered nuclear magnetic resonances are measured and MR images (for example) are reconstructed based thereon. For spatial coding of the measurement data, rapidly switched magnetic gradient fields are superimposed on the basic magnetic field. The acquired measurement data are digitized and stored in a k-space matrix as complex numerical values. An associated MR image can be reconstructed by means of a multidimensional Fourier transformation from the k-space matrix populated with such values.

In magnetic resonance imaging ("MRI") the breathing movement of a patient to be examined by means of MR can lead to artifacts known as ghosts ("ghosting"), and/or blurring and/or to intensity loss in the generated images, primarily in an examination of the organs of the thorax and the abdomen, thus of examination regions affected by the breathing movement of the patient. Additionally the breathing motion can lead to registration errors between generated images. These artifacts can hinder a finding on the basis of these images (for example by a physician) and can lead to the situation that lesions (for example) are overlooked.

Numerous techniques exist in order to reduce artifacts resulting from a breathing movement. Two groups of these techniques are known as respiratory gating and respiratory triggering, with these two terms not always being clearly separated.

Respiratory gating is an MR measurement during which the breathing of the patient is detected and associated with the acquired measurement data, wherein the repetition rate of the MR measurement (in particular its TR, thus the time between the successive excitation of a slice) is independent of the breathing of the patient. Rather, the repetition rate is controlled by a parameter or by an additional, different physiological signal, for example an ECG. The breathing information is then used (for example) to repeatedly acquire particular measurement data (packets)—that, for example, were acquired during strong breathing movement—until they have been acquired in a more quiescent phase of the breathing cycle. Another use of the breathing information can be to acquire k-space lines that are expected to be particularly movement-sensitive or k-space lines determining the image impression in an exceptional (quiet) breathing phase (what is known as "ROPE"—"respiratory ordered phase encoding").

Respiratory triggering is a technique that synchronizes an MR measurement (an imaging MR measurement, for example) with the breathing of the freely breathing patient and attempts to acquire defined packets of measurement data only during a marked phase of the breathing cycle. The marked phase is for the most part the relatively quiet phase of the breathing cycle at the end of the expiration. The acquisition of the measurement data is thus triggered by the phase of the breathing cycle. If a specific slice is hereby excited only once per trigger, the effective repetition rate (TR) of the measurement sequence is thus a whole-number multiple ($v=1, \ldots, k$) of the mean breathing cycle of the patient.

Respiratory gating and respiratory triggering are described in the article "Comparison of Respiratory Triggering and Gating Techniques for the Removal of Respiratory Artifacts in MR Imaging" by Lewis et al., Radiology 1986; 160:803-310, for example.

Furthermore, there are breath hold techniques in which the patient must hold his or her breath for the duration of the acquisition of the measurement data in order to avoid movement artifacts. One example of a repeated breath hold technique is described in the article by Wang et al., "Navigator-Echo-based Real-Time Respiratory Gating and Triggering for Reduction of Respiratory Effects in Three-dimensional Coronary MR Angiography", Radiology 1996; 198:55-60.

In the following respiratory triggering is discussed in detail. As noted, the respiratory triggering attempts to synchronize an MR measurement with the breathing cycle of a freely breathing patient and tries to limit the acquisition of image data to the relatively quiet phase of the breathing cycle at the end of the expiration. For this the breathing of the patient is detected as a physiological signal, for example, with a pneumatic sensor. After an initial learning phase of the trigger algorithm, a "trigger" is generated by the trigger algorithm as soon as the trigger algorithm detects a predetermined event. Initiated by such a "trigger", an MR sequence is executed that acquires an (again predetermined) portion of the measurement data from one or more slices. After this predetermined measurement data packet is acquired, the acquisition of the measurement data stops automatically until the trigger algorithm generates the next trigger. The second measurement data packet is thereupon acquired.

This workflow is continued until all measurement data of all slices are acquired. The predetermined event whose detection generates the trigger occurs when, for example, the last measured physiological signal crosses a threshold (set by an operator of the MR system) between the physiological signal (averaged over multiple breathing cycles) during maximum inspiration and the averaged physiological signal during maximum expiration. Triggers are normally generated only during the exhalation. In order that the acquisition of the measurement data can be limited to the relatively quiet phase of the breathing cycle at the end of expiration the following two conditions therefore must be fulfilled: on the one hand, a suitable threshold must be selected and on the other hand the acquisition duration of the predetermined measurement data packet must be brief relative to the individual breathing cycle of the patient.

The breathing cycle of the patient is typically between 3 and 6 seconds but is subject to significant individual (as well as illness-dependent) fluctuations. The acquisition duration of the measurement data packet depends on a number of parameters of the pulse sequence used for acquisition. In particular, in what is known as a multi-slice measurement, in which measurement data of different slices are acquired within one TR interval—on the number of slices from which measurement data are acquired after a trigger (i.e. within one measurement data packet). A very short acquisition duration per measurement data packet relative to the breathing cycle of the patient thereby reduces the efficiency (i.e. extends the total examination duration) since the number of breathing cycles that are needed in order to acquire all measurement data packets of all slices increases with decreasing amount of measurement data per breathing cycle. In the aforementioned example of a multi-slice measurement the efficiency therefore decreases with the decreasing number of slices from which measurement data are acquired per breathing cycle.

In contrast to this, if the acquisition duration per measurement data packet exceeds the duration of the relatively quiet phase at the end of the expiration, the acquisition of the measurement data also ensues during the subsequent inspiration. This can in turn lead to breathing artifacts or misregistration between slices. If the acquisition duration per measurement data packet reaches the duration of the breathing cycle or even goes beyond this, a trigger can, moreover, not be generated in every breathing interval but rather only in every second breathing interval, for example. This again increases the total examination duration and thus reduces the efficiency of the measurement.

In the prior art it is the task of an operator of an MR system to adapt parameters of the imaging MR sequence of an examination to the individual breathing cycle of a patient to be examined on the one hand and to input additional parameters on the other hand that describe the event that should initiate a trigger.

For example, in MR systems from Siemens it is known for an operator to first establish an acquisition window depending on a determined breathing cycle of the patient. The acquisition window is a time interval that upwardly limits the acquisition duration of measurement data per trigger. Values of parameters of an MR sequence that is to be used, such as the number of slices, repetition rate TR, turbo factor etc. are then limited such that the acquisition duration per trigger does not exceed the acquisition window. In Siemens MR systems the event that initiates the trigger is characterized by a parameter that describes a percentile threshold between the previously calculated average signal during maximum inspiration and the likewise pre-calculated average signal during maximum expiration. If a last measured physiological signal (breathing signal) exceeds this value, a trigger signal is initiated. The placement of the acquisition window is described in the Application Brochure for Body Imaging by Siemens AG in the chapter, "Application: Respiratory gating", Pages 110-113, for example. It is noted that the method designated there with "Gating" is a "triggering" according to the definition given above.

The approach in a Philips MR system is very similar to that by Siemens. There an acquisition window is likewise established by an operator depending on the determined breathing cycle of the patient. This is described in Chapter 2.24.2 "Respiratory triggering" on pages 2-46 through the top of 2-48 in the "Application Guide, Volume 2, Intera, Achieva, Panorama 1.0T, Release 1.5", for example.

In an MR system from GE an acquisition window but also a trigger position is to be set (among other things) as parameters for the implementation of a respiratory-triggered measurement. More detail is described in the chapter "Respiratory Gating and Triggering Parameters" on Pages 45-32 through 45-34 in "MR 1.5 Signa® EXCITE™ 11.0 Learning and Reference Guide" by GE, for example.

All leading manufacturers assist the operator in the task that was just described in that they visualize the measured physiological signal as a function of time and calculate and display the averaged breathing cycle of the patient. For example, the average breathing cycle is thereby defined as the average time interval between two successive extremes of the physiological signal during maximum inspiration.

Prerequisite for a respiratory triggered and respiratory gated MR measurement is the detection of the breathing movement as physiological signal. For this purpose breathing belts or cushions can be used, for example, that are placed on the patient and that detect (for example by means of pneumatic sensors) the rise and fall of his ribcage that are caused by the breathing.

An additional possibility for the detection of the breathing signal is the use of navigators. These are MR signals that are generated and received by means of the MR apparatus being used in addition to the actual MR signals for the desired MR examination (for example an imaging or spectroscopic examination). A navigator is normally a short sequence that, for example, acquires MR signals of the diaphragm from which (for example) the position of the diaphragm of the patient at a point in time of the navigator acquisition can be extracted. The diaphragm position can then be used as a physiological signal corresponding to a current breathing movement at the point in time of the navigator acquisition. The navigator sequence is interleaved with the imaging sequence and the breathing phase or position that is determined with the navigator measurement is assigned to the anatomical MR data directly acquired after said navigator sequence. This analogously applies for spectroscopic examinations.

However, given the use of navigators for respiratory triggering the problem results that the breathing cycle of the patient is generally still unknown during the measurement preparation since the breathing of the patient is first detected during the MR measurement. For an operator it is thus impossible to adapt the imaging parameters of the MR sequence to the individual breathing cycle of the patient, for example, or to optimally set the parameters that describe the desired trigger event before the beginning of the MR measurement.

In implementations of respiratory triggering with navigators in MR systems from Siemens AG the acquisition duration per trigger is graphically visualized, together with the detected physiological breathing signal, for the operator during a learning phase. The operator thereby has the possibility to terminate the MR measurement early given an unsuitable parameterization and to adapt it accordingly. This is described on Pages 20-27 in the aforementioned Application Brochure for Body Imaging by Siemens AG in the Chapter "Measurement during normal breathing—Navigator gating with 2-D PACE (I-IV)". However, in order to implement this procedure correctly a good training of the operator is required so that she has sufficient knowledge about the connections [relationships] of the parameterization and the breathing cycle.

Furthermore, in Siemens MR systems with what is known as "scout mode" the possibility is provided to implement a short MR measurement in which only the navigator sequence is deployed. The physiological breathing signal is visualized during this pure navigator measurement. As soon as a complete breathing period has been detected, the breathing cycle is calculated and displayed. The breathing cycle of the patient would therefore be known in turn during the preparation of the imaging sequence (for example) following the "scout mode" and can be used by the operator in setting the parameters of the imaging sequence. This is described on Page 108 in the aforementioned Application Brochure for Body Imaging by Siemens AG in the chapter "Application Navigator Gating—Optional measurement parameters (II)", for example.

Without an adaptation of the parameters of the MR measurement—thus the parameters that establish the type of acquisition of measurement data by means of magnetic resonance—only unsatisfactory results can be achieved for the most part. Particularly given patients in which measurement data from many slices are required to cover the organ to be examined, this frequently leads to the situation that the acquisition duration per trigger is significantly longer than the breathing cycle. As explained above, this leads to images with artifacts and to long examination times.

SUMMARY OF THE INVENTION

An object of the present invention to provide a method and a computer program that reduce movement artifacts in respiratory-triggered MR examinations, simplify a measurement preparation and keep a total duration of the MR examination as minimal as possible.

The method according to the invention for the acquisition of measurement data of a breathing examination subject by means of magnetic resonance hereby includes the following steps:

a) detect the physiological breathing signal of the examination subject with a breathing signal detection unit;

b) evaluate the detected breathing signal in an evaluation unit;

c) based on the evaluated breathing signal, calculate in a computer at least one parameter affecting the type of acquisition of measurement data by means of magnetic resonance;

d) detect a current physiological breathing signal with the breathing signal detection unit;

e) compare the last detected breathing signals with at least one trigger condition;

f) initiate the acquisition of measurement data using the calculated parameter of step c) upon satisfaction of the trigger conditions from step e);

g) repeat the steps d) through f) until all desired measurement data have been acquired; and h) store and/or process the acquired measurement data in a memory and/or processing unit.

After the evaluation of the detected breathing signal at least one parameter of a subsequent acquisition of measurement data is thus determined automatically without an input by a user or operator of the MR apparatus in use being necessary. The measurement data acquired in step f) are typically spectroscopic or imaging measurement data that should be acquired as a result of the MR examination. A preparation time required to prepare an MR examination is thus shortened. At the same time a possible faulty operation given an input of an operator is avoided. The at least one parameter is thereby matched to the individual breathing signal of the patient to be examined, whereby artifacts are avoided and the total duration of the MR examination is optimized. A training of operators can be done away with. An otherwise optional "scout mode" that is to be implemented separately as described above to check a navigator sequence in use or to determine an average breathing cycle can also be done away with.

In an exemplary embodiment of the invention the at least one parameter affecting the type of acquisition of measurement data by means of magnetic resonance is a parameter (beside other parameters) that determines the duration of the acquisition of measurement data after the triggering of the acquisition of measurement data. The duration of the acquisition of measurement data after the triggering of the acquisition of measurement data—thus after a trigger—in comparison to a cycle of the periodic breathing signal markedly affects the quality of the acquired measurement data.

In another exemplary embodiment the at least one parameter affecting the type of acquisition of measurement data by means of magnetic resonance is a maximum number of slices from which data are respectively acquired after a trigger. For example, in a multi-slice measurement the given number of slices to be measured is divided into groups such that the maximum number of slices per group does not exceed the maximum number of slices per trigger. After a trigger only data of slices that are associated with a group are then respectively acquired. In this way the duration of the acquisition of measurement data after a trigger can be controlled in a simple manner via the maximum number of the slices of the slices to be examined that are located in a group. If it is attempted to associate approximately the same number of slices with each group, the number of groups into which the slices to be measured are arranged can also effectively be considered as the at least one parameter affecting the type of acquisition of measurement data by means of magnetic resonance.

In one exemplary embodiment the at least one parameter affecting the type of acquisition of measurement data by means of magnetic resonance is a number of echoes of the echo train used for the acquisition of measurement data. The number of echoes in an echo train has a direct influence on the duration of the echo train, and therefore on the duration of the acquisition of measurement data after a triggering of an acquisition of measurement data.

In another exemplary embodiment, in a further step at least one trigger condition is calculated based on the evaluated breathing signal. In particular, the breathing signal is evaluated to the extent that a value of the breathing signal (trigger position) is determined; a trigger condition is satisfied upon reaching this trigger position, or upon falling below this trigger position, or if the deviation from this trigger position is less than a predetermined window value.

The invention also encompasses a non-transitory computer-readable storage medium encoded with programming instructions that, when the storage medium is loaded into a computerized operating and evaluation system of a magnetic resonance apparatus, cause the above-described method, including all embodiments thereof, to be executed.

DESCRIPTION OF THE PREFERRED EMBODIMENTS

Figure 1:
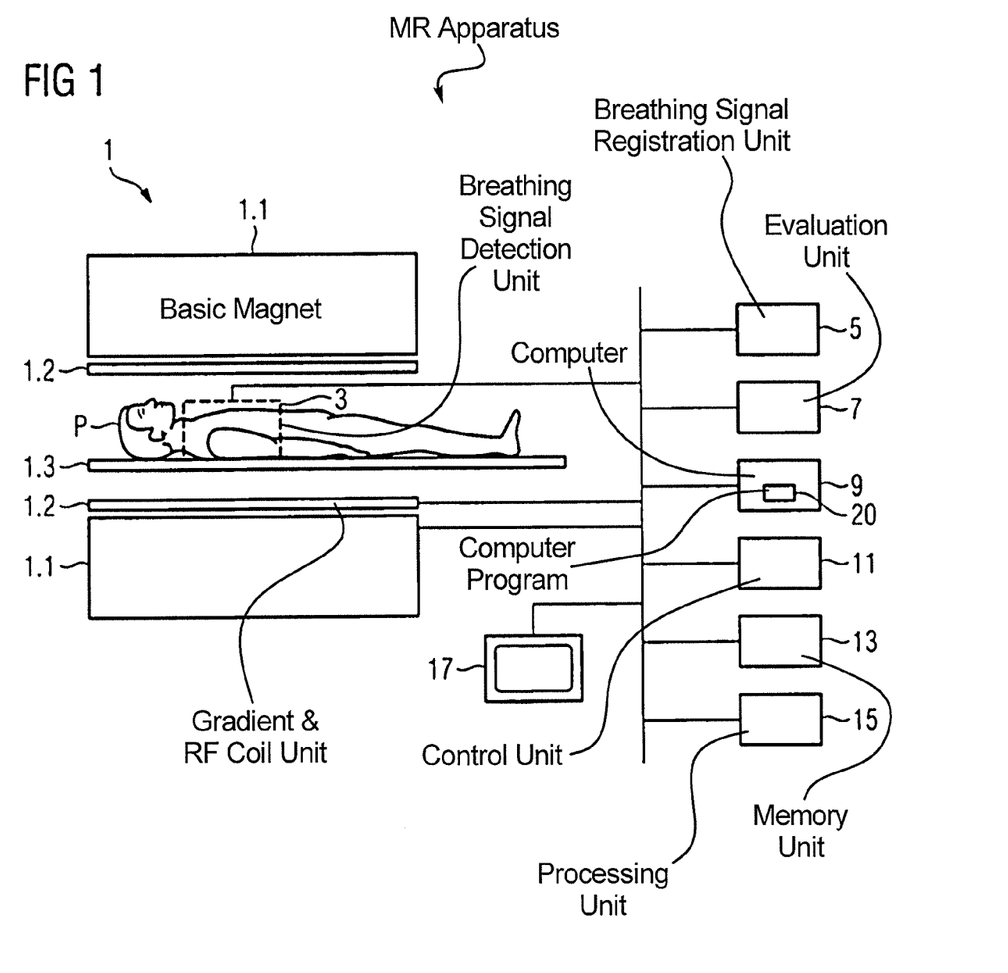
FIG. 1 schematically illustrates an MR apparatus with which the method can be implemented.

FIG. 1 is a schematic drawing of an MR apparatus 1 at which the method according to the invention can be implemented. The MR apparatus 1 is depicted using its basic magnet 1.1 and a gradient and RF coil unit 1.2 with which MR signals are generated in an examination subject (for example a patient) to be examined and can be acquired as measurement data. Additional components of an MR apparatus and its mode of operation are known and are not shown or explained in detail for clarity.

A patient P is supported on a patient support device 1.3 on which the patient can be driven into and out of the examination region of the MR apparatus 1. To detect his physiological breathing signal, a breathing signal detection unit 3—for example in the form of a breathing belt or a breathing cushion—has been placed on the patient. Alternatively, the breathing signal of the patient P can be detected directly by the use of navigator sequences by means of the MR apparatus 1, so additional hardware can be omitted and the patient can be situated on the patient support device 1.3 without additional limiting apparatuses on his body. In both cases the detected physiological breathing signal of the patient P is conducted to a breathing signal registration unit 5 and recorded there. The detected breathing signal is additionally conducted to an evaluation unit 7 in which it can be evaluated. For example, the evaluation of the detected breathing signal comprises a determination of local extremes in the detected breathing signal and/or a determination of a duration of a cycle in the detected breathing signal.

A computer 9 can access the evaluated breathing signal and, for example, calculate at least one parameter affecting the type of acquisition of measurement data based on the evaluated breathing signal.

For a breath-triggered MR measurement a current physiological breathing signal of the patient can also be detected with the breathing signal detection unit 5 and compared with at least one trigger condition in the computer 9, for example. If the at least one trigger condition is satisfied, an acquisition of measurement data using the calculated parameter is then initiated (triggered) by means of a control unit. The detection of the current physiological breathing signal, the comparison of this (and physiological breathing signal that were detected earlier) with the at least one trigger condition and the acquisition of measurement data, if the at least one trigger condition is satisfied, are hereby repeated until all desired measurement data (for example measurement data that completely reflect an organ to be examined) have been acquired.

The acquired measurement data can now be stored in a memory unit 13 and/or processed in a processing unit 15, for example converted into image data.

The breathing signal detection unit 5, the evaluation unit 7, the computer 9, the control unit 11 and the processing unit 15 can hereby store data in the memory unit 13 and retrieve it again.

The division of the different units that is selected here is not necessarily to be understood as a physical division but rather primarily as a purely illustrative division into figurative units. All cited units can be combined into a single physical unit or can be divided up in any other arbitrary manner or even be interconnected.

The detected breathing signal, a current breathing signal, image data and/or other data pertaining to the MR examination can be displayed at a display unit 17, for example.

A computer program 20 that implements a method according to the invention on the computer 7 when it is executed on said computer 7 can be executed on said computer 7.

Given the implementation of a method according to the invention to acquire measurement data of a breathing examination subject with the MR apparatus 1, the physiological breathing signal is, for example, initially detected over a length of multiple breathing cycles and then evaluated before other MR measurement data—for example imaging or even spectroscopic data—are acquired. This phase can be designated as a learning phase since here the individual breathing signal of the examination subject to be examined is "learned". This learning phase should not be chosen to be overly long since otherwise the total duration of the MR examination is accordingly extended. However, it should also not be selected to be overly short so that the individual breathing signal can be learned correctly. For example, if the duration of a breathing signal should be determined, it is necessary to detect the physiological breathing signal in the learning phase over at least one full breathing cycle. However, since the breathing signal of a breathing examination subject is not strictly periodical (rather it is subject to certain fluctuations) it is advantageous to even detect the physiological breathing signal over multiple breathing cycles in order to be able to take into account the fluctuations. This primarily applies since patients are often excited at the beginning of an examination and breath more quickly as a result of this. Therefore a learning phase of a length of 5 breathing cycles is recommended.

Figure 2:
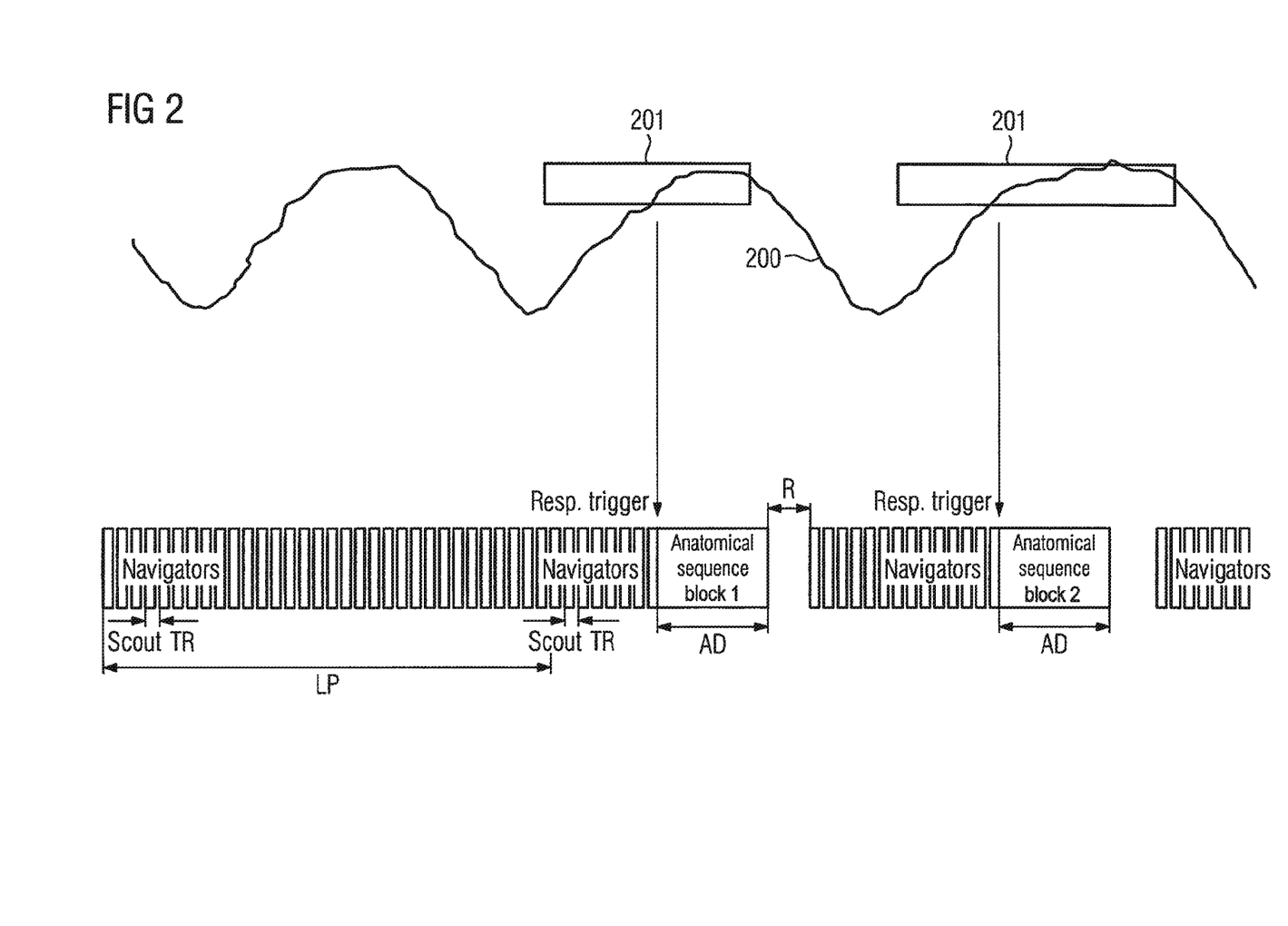
FIG. 2 schematically shows an example of a breath-triggered MR examination.

FIG. 2 is a schematic representation of an example of a breath-triggered MR examination, wherein the time curve of a sequence used for data acquisition is presented. The breathing signal in this example is detected by means of navigators. At the beginning of the sequence the navigator sequence is repeated with constant time interval scout TR ("Navigators") without interruption by an imaging or spectroscopic sequence until a sufficient number of physiological data points have been detected (this is described in greater detail further below, for example with regard to FIG. 6). This phase is the aforementioned learning phase ("LP")

An imaging phase (for example) of the MR examination begins after the learning phase "LP". In this imaging phase the navigator sequence is initially likewise repeated ("Navigators") with constant time interval ("Scout TR") and thus detects a current physiological breathing signal. The result of each navigator measurement is a respective physiological data point, for example a diaphragm position. The series of the last detected physiological data points allows conclusions of the current phase of the breathing. The series of the detected data points here is represented by a solid line 200 for illustrative purposes. In reality only one physiological data point is detected per navigator in the time interval of a "Scout TR". Consequently no physiological signal is present either at times at which no navigator sequence is executed. In spite of this, here it is represented as a solid signal 200 for a better understanding. As soon as a given trigger condition is satisfied ("Resp. Trigger"), no further navigator sequences are executed at first. Instead of this, the imaging sequence ("anatomical sequence block 1") is executed in the example shown in FIG. 2, meaning that an acquisition of measurement data (here imaging measurement data) is initiated and a first packet of measurement data is acquired. The triggering of the acquisition of the measurement data is designated in an abbreviated form as a trigger event in the following.

This process of the acquisition of measurement data occurs over a pre-established time interval ("Acquisition duration", "AD"). A specific, most often relatively short filling time "R" (for example of approximately 400 ms) can be inserted after the acquisition. For example, this filling time "R" can serve to allow a disruption of the magnetization in the examination subject that was caused by the imaging sequence to at least partially decay. This is advantageous since a disrupted magnetization can negatively affect the navigator measurement. The repetition of navigator sequences is then started anew until the trigger condition is satisfied a second time, normally preferred during the next breathing cycle of the patient. After the second trigger initiated in this manner, the imaging sequence acquires the second packet of measurement data ("anatomical sequence block 2"). This workflow is repeated until all image data are acquired.

A trigger is generated—meaning the acquisition of measurement data is initiated—if the trigger condition is satisfied. The trigger condition can be formed by multiple conditions that must all be satisfied. A condition can be, for example, that the patient exhales. With the sign convention that is used here this means that the result of the measured physiological data points is increasing. An additional trigger condition can, for example, be that the current (latest) measured physiological breathing signal is within in a pre-established acceptance window 201. In one exemplary embodiment the position of the acceptance window is automatically defined at the end of the initial learning phase LP based on the evaluated breathing signal.

Figure 3:
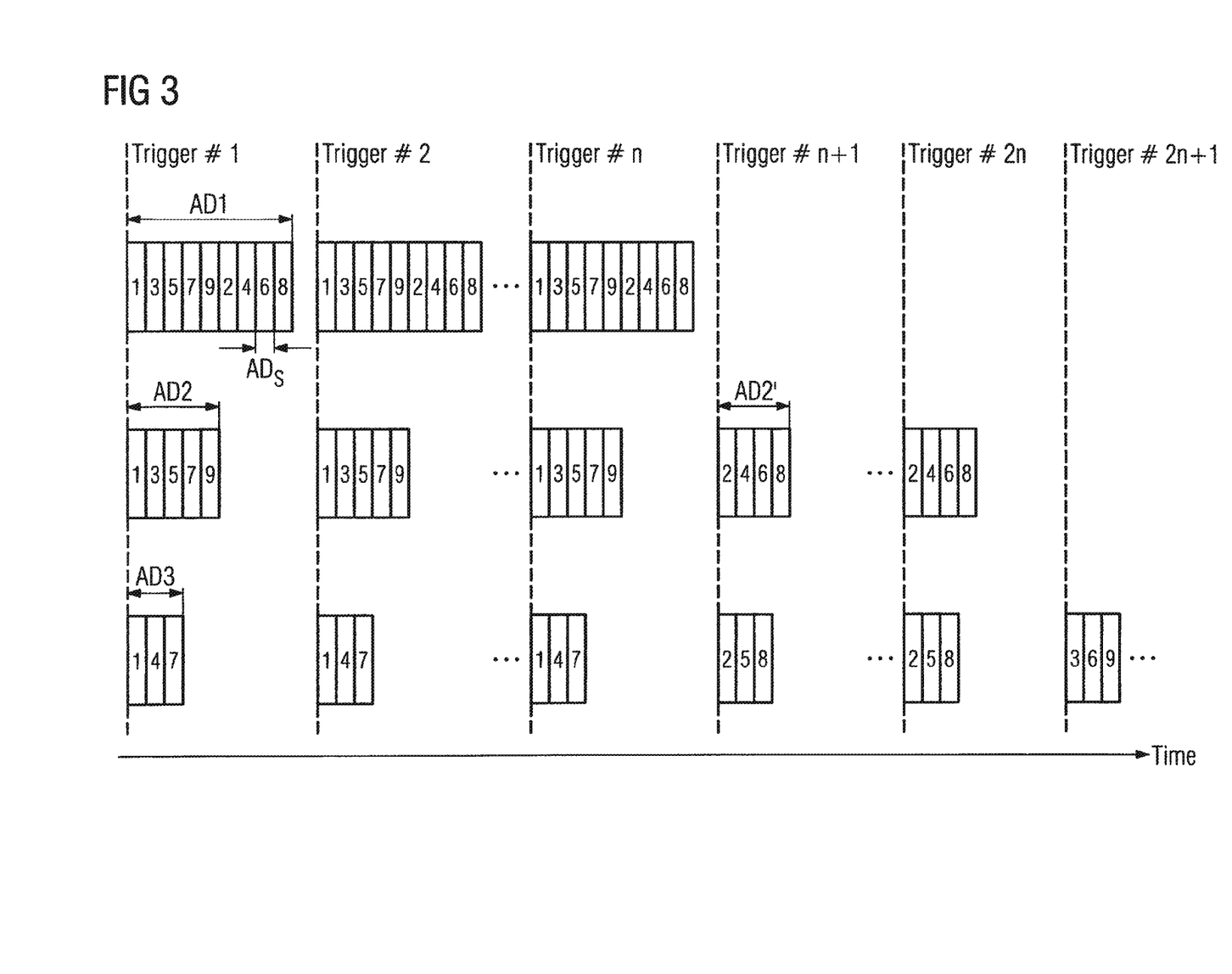
FIG. 3 illustrates the arrangement of the slices to be measured into groups affects the acquisition duration per trigger and the examination duration.

FIG. 3 is an exemplary illustration how a specific parameter affects the acquisition of magnetic resonance data in a respiratory triggered acquisition.

In order to cover an entire examination region with one 2D sequence, i.e. in order to acquire all measurement data necessary to show the desired examination region, the measurement data normally must be acquired in numerous slices into which the examination region is subdivided. The precise number of slices depends on the size of the examination region, the slice thickness and the separation of the individual slices from one another. For example, 20 to 40 slices are typically required in order to cover the organs of the abdomen (for example) and then to be able to show them in three dimensions. In respiratory-triggered MR techniques the effective repetition time (TR) of a sequence used to acquire the measurement data is determined by the breathing cycle of the patient (typically approximately 4-6 s). Therefore this technique is preferably used for sequence techniques with a comparably long repetition time. To avoid extreme long acquisition times (due to the long TR) an interleaved acquisition scheme is preferably used in turn in these sequence techniques. In an interleaved acquisition scheme corresponding measurement data of different slices are acquired before the excitation of a specific slice to acquire a next packet of measurement data is repeated. As an alternative to the interleaved acquisition scheme, what is known as a sequential data acquisition scheme can be used in which all measurement data of a slice are completely acquired before the acquisition of the measurement data of an additional slice is begun. The sequential 2D method is normally only used in connection with respiratory triggering, if the acquisition of one slice is so fast that all data of a slice can be acquired after one trigger. In this case the breath triggering serves to avoid registration errors between slices.

A possibility to adapt the acquisition duration ("AD") of an interleaved multi-slice measurement (here with nine slices in total as an example) to an individual breathing cycle of a patient is now illustrated in FIG. 3.

The interleaved acquisition scheme for the nine slices is shown in the upper row of FIG. 3. After each trigger the nine slices are excited in series and respective measurement data are acquired. To reduce the crosstalk of adjacent slices, as shown first all slices with odd slice index are thereby excited and subsequently all slices with even slice index are excited in a second pass. It is thereby assumed that the slices are indexed corresponding to their spatial position. Crosstalk is the fact that every radio-frequency pulse also unavoidably excites regions outside of the slice due to its finite duration. This implicit excitation primarily affects the nearest neighbors. With the two passes it is achieved that this implicit excitation of a slice with even slice index by its nearest neighbors (with odd slice index) has at least partially decayed at the point in time of its excitation (thus during the second pass). n excitations are necessary to completely acquire the data of a slice. The MR examination is thus concluded after n trigger events, thus, assuming one trigger per respiratory cycle, after n breathing cycles. The acquisition duration AD1 per trigger event—which should be markedly shorter than a breathing cycle to avoid artifacts, for example—here is nine times the acquisition duration per slice excitation $AD1=9*AD_S$.

A possibility to reduce the acquisition duration per trigger event, for example if a breathing cycle is in the range of the acquisition duration $AD1=9*AD_S$, is shown in the middle row of FIG. 3. For this the slices as they are shown in the middle row of FIG. 3 are arranged in two groups. The first group consists of all slices with odd slice index, for example, and the second group consists of all slices with even slice index. Here the measurement data of the first group are initially acquired completely before the acquisition of the measurement data of the second group is begun. n excitations—thus n trigger events—are necessary for the acquisition of the measurement data of each group (given otherwise unchanged parameters of the imaging sequence). Under the assumption of one trigger event per breathing interval, the total measurement duration thus doubles relative to the representation in the upper row. However, the acquisition duration AD2 per trigger event is markedly shortened with five times or, respectively, four times the acquisition duration ($AD2=5*AD_S$ or, respectively, $AD2'=4*AD_S$) per slice excitation. The maximum number of slices per group here is thus equal to five. The described division scheme of the slices into the individual groups again has the aforementioned advantage of the reduction of the crosstalk between adjacent slices and furthermore avoids contrast differences between adjacent slices that can occur as a result of different crosstalk. However, another type of division can also be chosen if needed.

If the breathing cycle limiting the acquisition duration is even shorter, the slices can also be divided into three groups (for example) as is visible in the lower row of FIG. 3. The acquisition duration AD3 here is thus 3 times the acquisition duration per slice excitation ($AD3=3*AD_S$). The maximum number of slices per group here is thus equal to three. A division of the slices into three (or in general C) groups analogously ensues in a simple manner, meaning that every third or, respectively, C-th slice is respectively associated with a group. The acquisition duration per trigger is analogously shortened with increasing number of groups and the total number of trigger events to acquire all measurement data of all slices increases with the number of groups.

A large number of groups therefore normally leads to few remaining movement artifacts since the data acquisition (given an optimal selection of the trigger point in time; not shown in FIG. 3) can be limited to a particularly quiet phase of the breathing cycle. A small number of groups normally shortens the examination duration insofar as the acquisition duration per trigger is markedly shorter than one breathing cycle. The optimal number of groups depends on the individual breathing of the patient. In the prior art it is adapted by an operator to the breathing cycle of the patient, with the disadvantages cited above. In the present invention it is determined automatically by the system, for example at the end of the learning phase.

The parameter "number of groups" that affects the type of acquisition of the measurement data has the advantage that it allows to vary the acquisition duration per trigger (AD), independent of the underlying sequence technique. Additionally it usually has only a slight influence on the image contrast. It can therefore be selected automatically without the measurement data achieved with it being negatively affected. Even a confirmation of an automatically chosen "number of groups" parameter by an operator can thus be omitted.

There are normally many additional parameters of an imaging or a spectroscopic sequence that affect the acquisition duration per slice excitation and thus the acquisition duration per trigger (given a constant number of slices per group or, respectively, groups C). Examples are the readout bandwidth per pixel, the echo train length given a turbo spin echo sequence (TSE) or the echo train length of an echoplanar sequence (EPI). However, these parameters normally also directly or indirectly determine the contrast of the reconstructed images. In some cases—given the "echo train length" parameter in a single shot sequence—the resolution of the reconstructed images can also be affected. However, contrast and resolution are decisive for the diagnostic value of the images reconstructed from the measurement data. Therefore an implicit change by the system is normally not accepted. Therefore additional adjustments (that normally are specifically matched to the respective sequence) are necessary in order to avoid a change of the contrast or the resolution. This should be explained in the following with reference to FIGS. 4 and 5 in an example of a variation of the echo train length of a turbo spin echo sequence.

Figure 4:
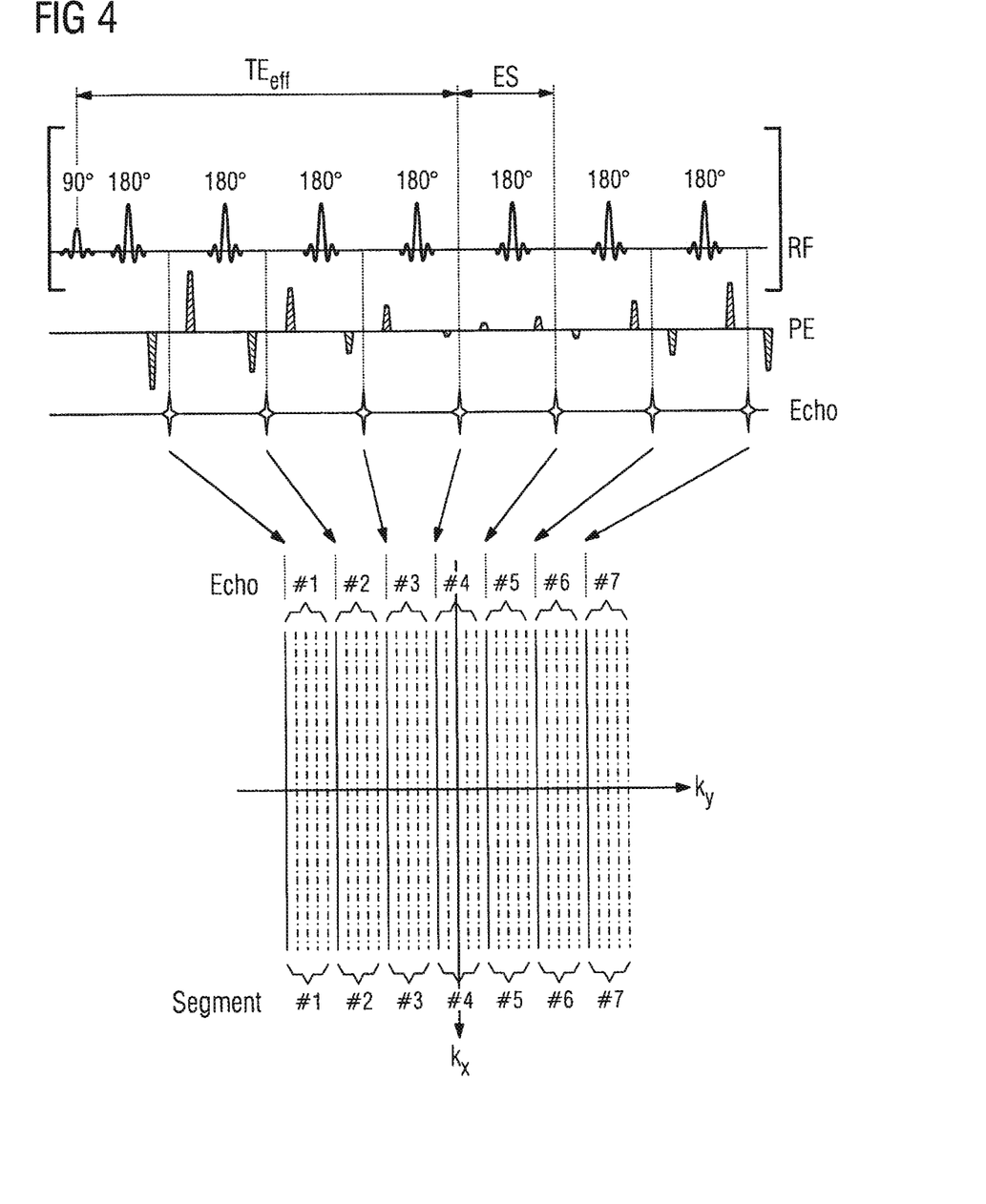
FIG. 4 schematically illustrates an echo train of a turbo spin echo sequence from the prior art.

FIG. 4 schematically shows an individual echo train of a turbo spin echo sequence as it is also used in the prior art, for example in the T2-weighted imaging in the abdomen.

An echo train is composed of a radio-frequency excitation pulse (here 90°) followed by a series of radio-frequency refocusing pulses (here 180°) as shown in the upper line "RF". As is shown in the third line "Echo", after each refocusing pulse a spin echo is generated at a time interval "ES" and a k-space line is respectively read out in its temporal environment and acquired as measurement data. As is typical in magnetic resonance technology, for this magnetic gradient fields are switched in a suitable manner for selective slice excitation, spatial coding of the acquired measurement signal and suppression of unwanted signal components. In FIG. 4 only the corresponding phase encoding gradients and phase refocusing gradients are schematically shown in the second line "PE" for the sake of clarity.

K-space to be filled with measurement data is shown in the lower region of FIG. 4. In the shown example 35 k-space lines (vertical solid and dash-dot lines) are to be filled. One k-space line is read out with each echo of an echo train and sorted along the $k_x$ direction of k-space. In the shown example with seven echoes per echo train, measurement data of seven lines are thus acquired with each echo train. In order to completely read out desired k-space from 35 k-space lines, five of the shown echo trains are therefore necessary. This corresponds to five trigger events since a respective echo train is initiated after a trigger event. An association between echo and k-space line ($k_y$ value) ensues via amplitude and polarity sign of the pair of respective phase encoding and phase refocusing gradients. This association is subject to a series of boundary conditions. Amplitudes and phase jumps in k-space should be minimal in order to avoid what are known as Gibbsian ring artifacts ("ringing artifacts") and ghosting artifacts. Due to the T2 decay along the echo train, echoes of different echo trains with the same echo index Echo #1 through #7 are therefore arranged in adjacent k-space lines. Seven segments #1 through #7 in k-space thus result with a respective line per echo train, thus five lines per segment. For clarification in the depiction the first line of a segment is respectively shown as a solid line and the four additional lines of the same segment are shown as dash-dot lines.

In order to minimize amplitude jumps between the segments, adjacent segments can be filled with successive echoes within the echo train. A stepped phase and amplitude modulation in k-space results from this association.

The k-space lines near the k-space center determine contrast and image impression. In the example these are respectively acquired from the fourth echo of the five echo trains. The echo time of the fourth echo thus determines contrast and image impression of the sequence. This is designated as the effective echo time $TE_{eff}$. The effective echo time is normally adjustable by the user.

As stated, an acquisition duration per trigger can be controlled in that the number of echoes of an echo train (also called the echo train length) is varied. A shortening of the echo train (fewer echoes per echo train) thereby goes along with an increase of the number of the echo trains or, respectively, trigger events that are necessary for complete acquisition of the measurement data; an extension of the echo train length (more echoes per echo train) normally goes along with a reduction of the number of echo trains or, respectively, trigger events necessary for complete acquisition of the measurement data when the total number of k-space lines in which measurement data are acquired is kept constant. The total number of k-space lines in which measurement data are acquired should at least not be reduced in order to not worsen the achieved resolution of the measurement data.

Furthermore, the k-space center must additionally be coded by echoes with the same echo index (echo index #4 in the example) in order to maintain contrast and image impression. In order to avoid artifacts, an optimally smooth amplitude and phase curve in k-space should be maintained.

Figure 5:
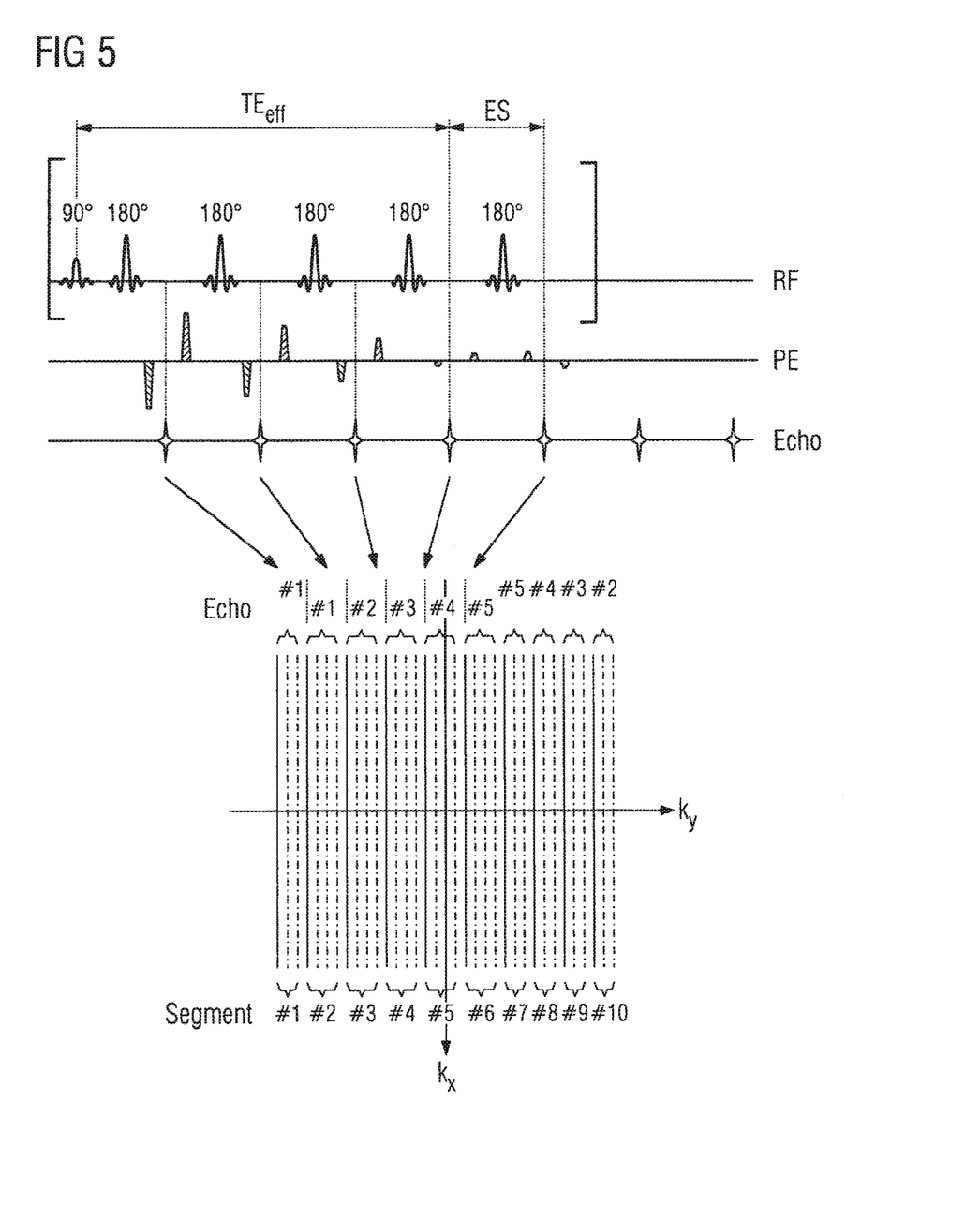
FIG. 5 schematically illustrates an echo train of a turbo spin echo sequence after adapting a parameter to an individual breathing.

FIG. 5 now schematically shows an echo train of a turbo spin echo sequence after adaptation of the parameter "number of echoes per echo train" to an individual breathing. An association scheme of k-space lines with echoes of echo trains is thereby shown that—as in FIG. 4—likewise covers 35 k-space lines and that thereby satisfies all of the aforementioned conditions, however with a shortened echo train length (now five echoes—echo #1 through #5—per echo train here instead of seven echoes per echo train as in FIG. 4).

In order to fill the 35 k-space lines, seven echo trains or, respectively, seven trigger events are thus necessary here. K-space is subdivided into 10 segments: segment #1 through #10. The segments #2 trough #6 respectively consist of four k-space lines. For example, these are filled with the echoes of the first four echo trains, such that a line of segment #2 is filled by an echo with index echo #1, a line of segment #3 is filled by an echo with index echo #2 etc.

Segment #5 contains the k-space center and is filled by echoes with index echo #4 in order to maintain the effective echo time $TE_{eff}$ without variation. The remaining segments #1 and #7 through #10 are filled with the remaining three echo trains (of the seven in total). Echoes with index echo #1 hereby fill the segment with segment index #1 (for an easier differentiation of k-space lines with the same echo index the echo index of k-space lines acquired with the last three echo trains are written offset slightly upward). The further association of echo index with segment ensues from the k-space periphery inward. Echoes with index echo #2 thus fill the k-space segment #10, echoes with index echo #3 fill the k-space segment #9 etc. Amplitude jumps between segment #6 and #7 (that in FIG. 5 are both filled with late echoes of the echo trains) are avoided with this association. Adjacent segments are thus respectively filled with echoes with the same echo index or an echo index deviating by only one position, whereby amplitude jumps are minimized.

Figure 6:
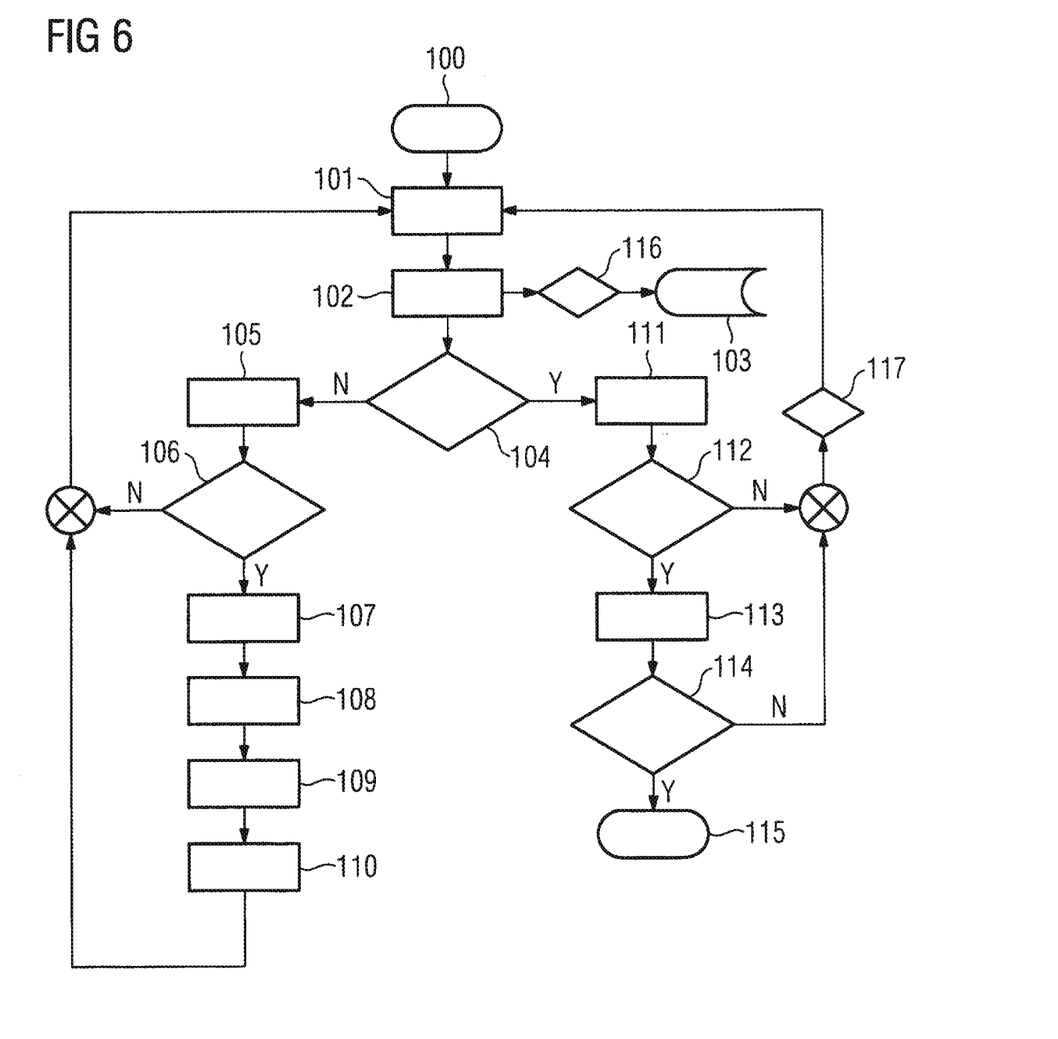
FIG. 6 schematically illustrates a flowchart of a method according to the invention.

FIG. 6 now shows a schematic workflow diagram of a method according to the invention.

If the method is started (Block 100), a detection of the physiological breathing signal of a breathing examination subject to be examined is initially started (Block 101). For example, the execution of a navigator sequence is begun or the signal of a breathing belt or breathing cushion that was previously placed on the examination subject is detected.

For a better processing capability, in Block 102 the primary detected signal is converted into a value pair consisting of a physiological value of the breathing signal and an associated time stamp. For example, in Block 102 a physiological data point (for example the position of the diaphragm) together with a point in time of the acquisition of the data by means of the navigator sequence is extracted from raw data acquired by a navigator sequence. Given the use of a breathing belt or breathing cushion, for example, the voltage read out at by a pressure sensor at a specific point in time—which voltage is proportional to the compression of the breathing belt or, respectively, breathing cushion—is converted into a digitally processable physiological signal. The time stamp associated with the physiological signal corresponds to the point in time of the readout of the voltage.

The extracted series of data points (physiological breathing signal with the associated time stamp) is stored in a global memory, for example. "Global" in this context means that multiple units that are used at various blocks in the workflow diagram have access to the memory 103.

In a query 104 it is interrogated as to whether the learning phase has already ended, i.e. whether a sufficient number of data points of the physiological breathing signal are stored in the memory 103. A sufficient number of data points can be determined via a predetermined value M of a minimum number of breathing cycles to be detected, for example, as is stated more precisely further below. At the start of the method (Block 100) this Boolean variable is set to "false". This means that the query 104 is answered with no ("N") after the detection of the first data point of the physiological breathing signal.

If the response to query 104 is "N", an evaluation of the detected breathing signal is begun, for example (Block 105). For this an evaluation unit access the global memory in read mode and reads out the already detected series of data points, for example in order to determine local extremes (minima and maxima) in this series. This occurs in a known manner, for example under calculation of at least one derivative of the series over time. Without limiting the generality, the following sign convention is agreed upon here: a local minimum corresponds to a state of maximum inspiration and a local maximum corresponds to a state of minimum inspiration.

Furthermore, in Step 105 at least one duration of a cycle in the detected breathing signal (one breathing cycle, also called a breathing interval) can also be determined. A breathing cycle is defined as, for example, the time interval from one state of maximum inspiration to the next state of maximum inspiration. The number of detected breathing intervals is thus equal to the number of local minima minus one. After this an additional query 106 can ensue that, for example, interrogates whether a predetermined value M of local minima (for example) has already been determined in the series of already detected physiological data points. As long as the number of detected breathing intervals is less than the predetermined value M, the query 106 is answered with "N" and the examination is continued with an additional detection of the physiological breathing signal, for example the acquisition of measurement data by means of a next navigator sequence (Blocks 101 and 102).

In particular if the physiological signal is detected by means of navigators, the time interval of successive navigator sequences should be the same so that the magnetization in the examination subject can achieve a dynamic steady state. This time interval (which corresponds to the "scout TR" from FIG. 2) should be selected to be long enough that both a navigator sequence can be executed in it and the measurement data acquired with the navigator sequence can be processed in it.

If the (M+1)-th local minima—thus the (M+1)-th state of maximum inspiration—is determined, the query 106 is answered with yes ("Y"). The detected physiological signal can thereupon be evaluated further (Block 107). For example, here a median of multiple durations of different cycles (which durations are determined in Block 105) are determined in the detected breathing signal. For example, this occurs in the following manner:

The series $(T_1, \ldots, T_{M+1})$ is the series of the time stamps of the detected physiological data points that were identified as local minima in the series of physiological data points. From this the series $A=(a_1, \ldots, a_M)$ is initially calculated. The n-th element of the series A is the duration of the n-th cycle in the detected breathing signal:

$$a_n = (T_{n+1} - T_n), n = 1, \ldots, M.$$

The series A is subsequently sorted according to the length of the breathing cycles. This new series here is designated with $B=(b_1, \ldots, b_M)$. B thus possesses the same elements as A; however, it applies that; $b_n \leq b_{n+1}$.

The median $\tilde{b}$ of the durations of the breathing cycles V then results as follows:

$$\tilde{b} = \begin{cases} b_{(N+1)/2} & N \text{ odd} \\ (b_{N/2} + b_{(N/2)+1})/2 & N \text{ even} \end{cases} \quad (1)$$

Alternatively, a different statistical value could also be calculated that reflects an "average" duration of a breathing cycle (not to be understood as a mathematical average but rather as a "normal" duration), for example the mean value of the calculated durations of the breathing cycles. The resorting of the series A into the series B could hereby be omitted. However, relative to the mean value the median has the advantage that it is more robust relative to "outliers", wherein what are understood by "outliers" here are individual durations of breathing cycles that are significantly longer or significantly shorter than the remaining breathing intervals. In the following the median of the durations of the breathing cycles is therefore always discussed, without this representing a limitation.

At least one parameter affecting the type of acquisition of measurement data by means of magnetic resonance can now be calculated on the basis of the evaluated breathing signal (Block 108). For example, for this the median of the durations of the breathing cycles (which median was determined in the evaluation of the physiological breathing signal) is passed to a computer and from this a number of groups C into which a number of slices necessary for the examination should be divided up is calculated as a parameter, as was already explained in regard to FIG. 3.

For example, this occurs in that the smallest number of groups C is selected for which it applies that an acquisition duration per trigger AD is less than a percentile proportion D of the median $\tilde{b}$ of the durations of the detected breathing cycles:

$$AD \leq (D/100) * \tilde{b} \qquad (2)$$

This means that the parameter C should be selected such that the acquisition duration per trigger AD does not exceed a specified percentile proportion of the determined individual breathing cycle.

The calculation of the parameter affecting the type of acquisition of measurement data by means of magnetic resonance thus comprises a calculation of a percentile proportion of a duration of a cycle of the detected breathing signal $(D/100)*\tilde{b}$ that is determined in the evaluation of the detected breathing signal.

$(D/100)*\tilde{b}$ thus limits the maximum acquisition duration per trigger AD. D is thereby a (normally) patient-independent, predetermined value (i.e. a value that is not to be adapted to an individual breathing of the patient) between 1 and 100. Practical values typically lie between 25 and 50. The specification of the percentile proportion as (D/100) merely serves to illustrate that it is a percentile proportion. Naturally a value d can also be predetermined for which it applies that: d=(D/100).

The value D is, for example, predetermined by a person attending the acquisition of measurement data by means of magnetic resonance. Alternatively, D can also be an empirical value set depending on an acquisition type (for example a chosen sequence) selected for the acquisition of the measurement data.

Specification by a person attending the acquisition of the measurement data allows the value to be chosen between the opposing advantages of a short examination duration (large value D) or, respectively, few remaining movement artifacts (small value D), for example. In contrast to this, if an empirical value is used that cannot be modified by the user it is preferably selected depending on the underlying imaging or spectroscopic sequence. For example, a larger value can be selected given a relatively motion-insensitive PROPELLER sequence than given the motion-sensitive Cartesian variant of the same sequence.

As an alternative to the limitation of the maximum acquisition duration per trigger AD by such a predetermined, percentile proportion of a determined duration of a breathing cycle, the maximum acquisition duration per trigger AD can also be determined directly from the detected physiological breathing signal. [sic] For example, in that a maximum time interval is determined in which a maximum or average variation of the physiological breathing signal does not exceed a fixed, selected value or a percentile proportion of a maximum or average variation between signal values of at least one inspiration and signal values of at least one expiration in the detected breathing signal. An absolute variation or a variation relative to the variation of the physiological breathing signal is thus provided, and a maximum time interval is sought in which the variation of the signal does not exceed the predetermined variation. In general, the variation within the time interval increases with the duration of the time interval. The maximum time interval sought here then specifies the maximum acquisition time per trigger.

As discussed with regard to FIG. 3 in an interleaved multi-slice measurement the maximum acquisition duration per trigger AD proportional to the maximum number of slices per group. Given an association of the slices to be measured with groups AD thus depends on the number of groups C. AD is hereby at maximum the number of slices S from which measurement data should be acquired divided by the number of groups C, rounded to the next whole number, times the acquisition duration per slice excitation $$AD_S: AD \leq \left\lceil \frac{S}{C} \right\rceil * AD_S,$$

wherein $\lceil \bullet \rceil$ stands for the rounding function. The at least one parameter affecting the type of acquisition of measurement data by means of magnetic resonance—here the number of groups C—is thus dependent on the patient-independent value D and the patient-dependent median of the duration of a breathing cycle.

According to the inequality (2), the calculation of the number of groups C into which the required number of slices S is divided comprises a comparison of the acquisition duration of the measurement data of the slices of a group per trigger with the statistical duration of a cycle of the detected breathing signal, which statistical duration was determined in the evaluation of the detected breathing signal.

If the inequality (2) cannot be satisfied for all possible values of C, the number of groups is set equal to the number of slices.

The type of acquisition of the measurement data is now controlled via a control unit so that the sequence used for the acquisition of the measurement data is prepared for the new group count C or, respectively, a preparation that has already occurred is adapted to the new group count. "Preparation" includes all calculations that can ensue before the actual sequence start. Thus among other things the calculation of the slice excitation order, the calculation of filling times, etc.

As is described in relation to FIGS. 4 and 5, an alternative or additional parameter affecting the type of acquisition of the measurement data can also be a number of echoes per echo train that is used. In this case inequality (2) continues to apply; however, here the acquisition duration per slice excitation $AD_S$ is dependent on the number of echoes E per echo train that is used: $AD_S = E*ES+K$, wherein ES stands for the echo interval and K stands for all additional sequence-dependent times such as a duration of the excitation pulse that is used, duration ES/2 between excitation pulse and first refocusing pulse and possible other times, for example duration of possible spoiler gradients, etc.

It furthermore applies that $$AD \leq \left\lceil \frac{S}{C} \right\rceil * AD_S.$$

Both a number of groups C and a number of echoes E per echo train can thus also be respectively calculated as a parameter affecting the type of acquisition.

Just the parameter "echoes per echo train" can also be calculated. In particular this is a useful option, if the total number of slices to be acquired is one: S=1. S=1 is typical for a 3D sequence in which the examination region is normally (but not necessarily) covered completely by a single excitation volume, for example. For S=1 a method described with regard to FIG. 3 cannot be used since a single slice cannot be divided up into groups. For MR examinations with S=1 it then applies that AD is approximately equal to E*ES+K.

After the acquisition duration per trigger AD has been selected automatically (via inequality (2) and the parameter affecting the type of acquisition of the measurement data) so that AD is matched to the individual breathing signal, at least one trigger condition can furthermore be calculated based on the detected breathing signal (Block 109).

For example, what is known as a trigger position TP (or threshold) can be calculated. The trigger position TP has the same units as the physiological breathing signal. A trigger is only generated when, for example, a deviation of a data point of a last measured, current physiological breathing signal from the trigger position TP is less than or equal to a predetermined acceptance window [TP−δ, . . . , TP+δ], where δ is a predetermined window value. Alternatively, a trigger can only be generated when the current physiological breathing signal exceeds (using the aforementioned sign convention) the trigger position.

The calculation of the trigger position can ensue as follows, for example: $P=(p_1, \ldots, p_L)$ is the series of measured physiological data points. M+1 elements of this series P were also identified in Block 105 as states of maximum inspiration. $I=(i_1, \ldots, i_{M+1})$ is the series of indices that addresses states of maximum inspiration. In words:

$p_{i_k}$ (1<=k<=M+1) is the value of the data point of the detected physiological breathing signal during the k-th state of maximum inspiration that was detected at point in time $T_k$. There is always a state of maximum expiration between two respective states of maximum inspiration. The corresponding data points of the detected physiological breathing signal are addressed by a second index series $E=(e_1, \ldots, e_M)$. Furthermore, a function t can associate a signal point with its time stamp. With the definitions that have previously been made it this applies that:

$$T_k = t(p_{i_k}) < t(p_{e_k}) < t(p_{i_{k+1}}) = T_{k+1}, k=1, \ldots, M$$

A trigger position $TP_k$ can now be initially determined as follows for each of the M breathing intervals of the detected breathing signal.

In one embodiment, the acquisition duration per trigger AD that is calculated in Block 108 is used in order to calculate the trigger position TP on the basis of the acquisition duration per trigger AD (and therefore depending on the parameter affecting the type of acquisition of the measurement data) and on the basis of the detected breathing signal.

For a given AD and Scout-TR, ad is defined as the smallest whole number for which it applies:

$$ad \geq AD/\text{Scout } TR.$$

Scout TR is thereby the constant time interval between two successive physiological data points:

$$\text{Scout } TR = t(p_{i+1}) - t(p_i).$$

ad therefore corresponds to the number of successive data points of the detected physiological breathing signal that was detected in a time span that covers the acquisition duration per trigger AD.

For the data points with index j in the interval $i_k <= j <= e_k$ that thus lie between a maximum inspiration and a maximum expiration (and therefore in a phase of the expiration), the following sum, which is a measure of a "flatness" of the curve of the appertaining data points of the detected breathing signal, can now be calculated:

$$\text{Sum}(j) = \sum_{i=j}^{j+ad} (p_i - p_{e_k})^2.$$

$j_{min}$ is the index in the interval $i_k <= j <= e_k$ that minimizes the sum Sum(j), i.e. the index of the data point as of which the "flattest" curve exists across the following ad data points:

$$j_{min} = \min_{j=i_k}^{e_k} \{\text{Sum}(j)\}$$

The trigger position $TP_K$ for the k-th breathing interval is now set equal to the physiological signal value of the data point with index $j_{min}$, thus: $TP_k = p_{j_{min}}$.

In order to obtain a more stable trigger position TP, a current trigger position TP can now be set as the median of the M trigger positions $TP_k$. The calculation of the median was already shown further above in the example of the median of durations of breathing cycles. The median is calculated analogously for the trigger position.

The trigger position TP here thus corresponds to a value of the breathing signal; upon reaching it a trigger condition is satisfied within the scope of a predetermined deviation (acceptance window).

The learning phase is at the latest concluded with the calculation of at least one trigger condition (Block 109) and the Boolean variable of query 104 is set to "true" (Block 110). The measurement is now located in the imaging or spectroscopic phase. After a further run-through of Blocks 101 and 102 in which a current physiological breathing signal is detected, the query 104 is now answered with "Y" and a control unit (that in particular comprises a trigger unit) compares the last detected breathing signals with at least one trigger condition (Block 111).

The deployment of the navigator sequence with constant time interval Scout TR (Block 101) and the associated conversion of the detected signal into a physiological data point (Block 102) is continued until the situation that the trigger conditions have been satisfied is first established in Block 111 (Query 112: trigger condition satisfied Y/N?). In order to generate a trigger event, in one embodiment at least the following two conditions are satisfied:

1) The series of the last detected physiological data points must be increasing, which corresponds with the sign convention of a phase of exhalation that was made.

2) The deviation Δ of the last measured physiological signal point from the trigger position TP must be less than or equal to a previously established acceptance window [TP−δ, . . . , TP+δ], i.e. $|\Delta| \leq \delta$.

If the trigger condition is satisfied, an acquisition of measurement data is initiated by the trigger unit. This means that a trigger event is generated and a first packet of imaging or, respectively, spectroscopic measurement data is acquired per trigger. The duration of the acquisition of this data packet is AD and is matched to the individual breathing cycle via the calculated parameter affecting the acquisition of measurement data. What is to be understood by a packet hereby depends on the underlying imaging or, respectively, spectroscopic sequence. For example, given a T2-weighted turbo spin echo sequence a packet can consist of one respective echo train per slice of the first group.

After acquisition of the first packet of measurement data the measurement is continued with the deployment of additional navigator sequences until the trigger condition is satisfied a second time. After the second trigger event is initiated in this manner a second packet of measurement data of the imaging or spectroscopic sequence is acquired. This workflow is continued until all measurement data of the desired examination region to be examined are acquired (Query 114: all measurement data acquired Y/N?).

In particular given the acquisition of the current breathing signal by means of navigators, the interruption of the series of navigators (see also "Navigators" in FIG. 2) by a trigger event can disrupt the dynamic steady state of the magnetization. This can have a negative influence on physiological breathing signals extracted from the navigator signal immediately after the restart of the navigator sequences. For example, signal changes in such navigator signals can occur whose cause lies in the transcendent state of the magnetization during the resumption of the steady state. Such signal changes cannot be differentiated from signal changes as a result of the physiological breathing movement. This can thus adulterate the detected current breathing signals and thus lead to false trigger events.

However, these problems can be reduced by the following measures.

For example, after a trigger event and after the acquisition of measurement data a short (relative to the duration of a breathing cycle) filling time can be inserted before a next navigator sequence is executed to detect a physiological data point. During the filling time the magnetization in the examination subject partially relaxes. An example of such a filling time is designated with "R" in FIG. 2.

Furthermore, in a query 116 (for example by means of a counter) the number of the data point of the current breathing signal that is presently detected in Block 102 after a trigger event can be polled. If such a counter of a data point is smaller than a predetermined value Z, the data point can be discarded, meaning that it is not stored in memory 103. The predetermined value Z is a whole number and should be selected such that, for example, on the one hand the steady state can already have been at least approximately achieved again and on the other hand not too many data points have been discarded so that a trigger event can be generated in the following breathing interval. For example, if Z=2 the respective two first data points that are detected after resuming the navigators after a trigger event are discarded.

Given detection of the breathing signal with an external sensor (such as a breathing cushion or a breathing belt), such measures are normally not required since the signal of these sensors is normally not disrupted by the imaging or, respectively, spectroscopic sequence.

Furthermore, in one exemplary embodiment the following trigger condition must be satisfied in order to generate a trigger event after the query 112:

3) If a first trigger event has already occurred, a predeterminable time period $T_t$ must have passed since the last trigger event. For example, the time period $T_t$ is hereby greater than 60% of the median of the breathing cycle that is calculated in Block 107.

At least the duration of one breathing cycle normally lies between two trigger events since a trigger event is normally generated only once per breathing cycle. Two trigger events should thus not be situated significantly closer to one another than a percentile proportion of the calculated median of the breathing cycle that can be viewed as falling under a normal fluctuation of a duration of the breathing cycle.

In a further embodiment the calculation of the trigger position that is described above can possibly also be recalculated as a new trigger position TP' after conclusion of the initial learning phase and replace a trigger position TP (calculated in or at the end of the initial learning phase) for a next comparison of a current breathing signal in Block 111.

For example, this occurs as follows:

A query 117 monitors whether a trigger was generated between the last two detected states of maximum inspiration. Alternatively, the query 117 can monitor how much time has passed since a last trigger event, for example. If a next trigger event does not occur within the duration of one breathing cycle (possibly under consideration of normal fluctuations of said breathing cycle), thus within a duration $b_{max}$, the query 117 initiates a recalculation of the trigger position in Block 109. However, as described above the new trigger position TP' is thereby calculated as at the end of the learning phase, however based on (for example) the M last completely detected breathing cycles. After the first initiation of the recalculation this ensues on the basis of the last M−1 breathing cycles of the learning phase and the breathing cycle during which no trigger was generated, for example. Under the specified conditions the trigger condition "trigger position" is thus calculated again at least one additional time after a first calculation during the initial learning phase.

In an advantageous embodiment the parameter affecting the acquisition of the measurement data is not adapted together with the trigger position, meaning that in the above example the acquisition duration is not recalculated per trigger. In general this would have the consequence that a portion of the measurement data (imaging measurement data, for example) that have already been acquired would have to be discarded since a modification of the parameter affecting the acquisition of the measurement data during the data acquisition can lead to artifacts or contrast differences.

In an alternative query 117 the recalculation of the trigger position is initiated, if the time since the last trigger event exceed a threshold $b_{max}$. $b_{max}$ can be set, for example, equal to the duration of the calculated median of the breathing cycle $\tilde{b}$ times a factor $(1+\kappa)$, i.e. $b_{max} = (1+\kappa)\tilde{b}$, wherein $\kappa$ accounts for the extension that is permissible under a normal fluctuation of the breathing signal.

Such a recalculation of the trigger position is advantageous if the breathing of the patient changes during the examination. For example, some patients breath faster and/or deeper at the beginning of an MR examination, for example because they are agitated. A faster breathing leads to a shorter breathing cycle. AD is thus longer in comparison to the breathing cycle for a given acquisition time per trigger AD, whereby the trigger position is shifted downward. The breathing can also vary because the patient falls asleep during the examination. Via the recalculation of the trigger position this change can be taken into account even during the running MR examination, which improves the results of the MR examination and can shorten the total duration of the MR examination.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring magnetic resonance measurement data from a breathing examination subject, comprising the steps of:
    (a) detecting a physiological breathing signal of an examination subject using a breathing signal detection unit, to obtain a detected breathing signal;
    (b) in a computerized evaluation unit, automatically evaluating the detected breathing signal to obtain an evaluation result;
    (c) in a computerized processor, automatically calculating, based on said evaluation result, at least one parameter for operating a magnetic resonance data acquisition unit that has an effect on acquisition of magnetic resonance data from the examination subject by the magnetic resonance data acquisition unit;

(d) detecting a current physiological breathing signal from the examination subject with said breathing signal detection unit;

(e) in a computerized comparison unit, comparing the last physiological breathing signals that were detected with said breathing signal detection unit with at least one trigger condition, to obtain a comparison result;

(f) from said comparison unit, automatically initiating acquisition of said magnetic resonance data from the examination subject by said magnetic resonance data acquisition unit using said at least one parameter calculated in step (c), upon said comparison result indicating satisfaction of said at least one trigger condition by said last physiological breathing signals; and (g) repeating steps (d) through (f) until all desired magnetic resonance data have been acquired.

2. A method as claimed in claim 1 wherein step (c) comprises calculating at least one parameter that affects or determines a duration of acquisition of said magnetic resonance data after triggering said acquisition of said magnetic resonance measurement data.

3. A method as claimed in claim 2 wherein step (c) comprises calculating said at least one parameter depends on a percentile proportion of a duration of a cycle of the detected breathing signal, and statistically determining said duration of said cycle as said evaluation result in step (b).

4. A method as claimed in claim 3 wherein step (c) comprises calculating said at least one parameter as the maximum number of slices of the examination subject from which said magnetic resonance data are acquired after initiating said acquisition of said magnetic resonance measurement data in step (f).

5. A method as claimed in claim 4 comprising calculating said maximum number of slices comprises comparing a duration required for acquisition of magnetic resonance data for each slice of the examination subject with said statistical duration of said breathing cycle.

6. A method as claimed in claim 2 comprising calculating said at least one parameter as a number of echoes of an echo train used by said magnetic resonance data acquisition unit to acquire said magnetic resonance measurement data.

7. A method as claimed in claim 1 comprising calculating said at least one parameter dependent on a predetermined value that is provided to said computerized processor.

8. A method as claimed in claim 7 comprising manually providing said predetermined value to said computerized processor.

9. A method as claimed in claim 7 comprising selecting said predetermined value dependent on a type of data acquisition procedure used for said acquisition of said magnetic resonance measurement data from said examination subject.

10. A method as claimed in claim 1 comprising calculating said at least one parameter dependent on a maximum time interval of the detected physiological breathing signal in which a maximum or average variation of said physiological breathing signal does not exceed a fixed, selected value or a percentile proportion of a maximum or average variation between values occurring for at least one inspiration and values occurring for at least one expiration in the detected breathing signal.

11. A method as claimed in claim 1 comprising, in said computerized processor, calculating said at least one trigger condition dependent on the detected breathing signal obtained in step (a).

12. A method as claimed in claim 11 comprising calculating a trigger position and setting at least one trigger condition as satisfied, if said current signal exceeds said trigger position or said current signal falls below said trigger position or if the deviation between said current signal and said trigger position is less than a predetermined window value.

13. A method as claimed in claim 12 comprising calculating said trigger position by searching for a flat curve path of said detected breathing signal.

14. A method as claimed in claim 13, whereby the searched flat curve path lasts at least as long as the duration of acquisition of said magnetic resonance data after triggering said acquisition of said magnetic resonance measurement data.

15. A method as claimed in claim 13 comprising searching said flat curve path as a flat curve path that occurs in an exhalation phase of the detected breathing signal.

16. A method as claimed in claim 11 comprising calculating said at least one trigger condition dependent on said at least one parameter.

17. A method as claimed in claim 1 wherein step (e) comprises comparing the last physiological breathing signals with multiple trigger conditions and, in step (f) initiating the acquisition of the magnetic resonance measurement data when said comparison result indicates that all of said multiple trigger conditions are satisfied by said last physiological breathing signals.

18. A method as claimed in claim 1 wherein step (b) comprises evaluating the detected breathing signal by an evaluation procedure selected from the group consisting of determining local extremes in the detected breathing signal, determining a duration of a cycle in the detected breathing signal, determining a median value of multiple durations of different cycles in the detected breathing signal, determining an average value of multiple determined durations of different cycles in the detected breathing signal, and determining a statistical value, other than a median value or average value, of multiple determined durations of different cycles in the detected breathing signal.

19. A method as claimed in claim 1 comprising, in step (e) employing a trigger condition selected from the group consisting of said current detected breathing signal is in an exhalation phase, said current detected breathing signal is in a predetermined acceptance window and at least one time interval, having a length dependent on a statistically determined duration of a breathing cycle, has elapsed between the current physiological signal and a last initiation of acquisition of said magnetic resonance measurement data.

20. A method as claimed in claim 1 comprising electronically storing respective detected physiological breathing signals detected in repetitions in step (g) as data points, subject to a storage condition.

21. A non-transitory computer-readable storage medium encoded with programming instructions, said storage medium being loaded into a computerized operating and evaluation system of a magnetic resonance apparatus, and said programming instructions causing said computerized operating and evaluation system to:

(a) detect a physiological breathing signal of an examination subject using a breathing signal detection unit, to obtain a detected breathing signal;

(b) evaluate the detected breathing signal to obtain an evaluation result;

(c) calculate, based on said evaluation result, at least one parameter for operating a magnetic resonance data acquisition unit that has an effect on acquisition of magnetic resonance data from the examination subject by the magnetic resonance data acquisition unit;

(d) detect a current physiological breathing signal from the examination subject with said breathing signal detection unit;
(e) compare the most recent physiological breathing signals that were detected with said breathing signal detection unit with at least one trigger condition, to obtain a comparison result;
(f) automatically initiate acquisition of said magnetic resonance data from the examination subject by said magnetic resonance data acquisition unit using said at least one parameter calculated in step (c), upon said comparison result indicating satisfaction of said at least one trigger condition by said most recent physiological breathing signals; and
(g) repeat steps (d) through (f) until all desired magnetic resonance data have been acquired.

* * * * *